(12) United States Patent
Marotta et al.

(10) Patent No.: US 11,300,517 B2
(45) Date of Patent: Apr. 12, 2022

(54) METHOD FOR IMAGING A BIOLOGICAL SAMPLE AND CORRESPONDING PROBE

(71) Applicant: FONDAZIONE ISTITUTO ITALIANO DI TECNOLOGIA, Genoa (IT)

(72) Inventors: Roberto Marotta, Milan (IT); Tiziano Catelani, Serra Riccò (IT); Mauro Moglianetti, Civitanova Marche (IT); Elisa De Luca, Lecce (IT); Pier Paolo Pompa, Lecce (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 87 days.

(21) Appl. No.: 16/774,419

(22) Filed: Jan. 28, 2020

(65) Prior Publication Data

US 2020/0166463 A1    May 28, 2020

Related U.S. Application Data

(63) Continuation of application No. PCT/IT2018/050142, filed on Jul. 27, 2018.

(30) Foreign Application Priority Data

Jul. 28, 2017    (IT) .................. 102017000087291

(51) Int. Cl.
*G01N 21/64* (2006.01)
*B82Y 35/00* (2011.01)

(52) U.S. Cl.
CPC .......... *G01N 21/6486* (2013.01); *B82Y 35/00* (2013.01); *G01N 21/6458* (2013.01); *G01N 2223/418* (2013.01)

(58) Field of Classification Search
CPC ............... B82Y 35/00; G01N 21/6458; G01N 21/6486; G01N 2223/418; G01N 33/533; G01N 33/54346; G01N 33/582; G01N 33/587; G01N 33/68
See application file for complete search history.

(56) References Cited

FOREIGN PATENT DOCUMENTS

EP    1 801 593    6/2007

OTHER PUBLICATIONS

Deborah Pedone et al; Platinum nanoparticles in nanobiomedicine, Chemical Society Reviews, vol. 46, No. 16, Jul. 11, 2017, pp. 4951-4975.
Victoria Liss et al.; Self-labeling enzymes as universal tags for fluorescence microscopy and electron microscopy; Scientific Reports, vol. 5, No. 1, Dec. 8, 2015.

(Continued)

*Primary Examiner* — Mark R Gaworecki
(74) *Attorney, Agent, or Firm* — Reinhart Boerner Van Deuren P.C.

(57) ABSTRACT

Imaging method for a biological sample using microscopy, for example fluorescence optical microscopy, electron microscopy, or correlative microscopy, which provides to use imaging probes to obtain images in which it is possible to identify the imaging probes and/or possible molecules associated with them. The present invention also concerns the imaging probes, possibly functionalized, that can be used both in CLEM experiments and also in immunocytochemical experiments.

15 Claims, 1 Drawing Sheet

(56) References Cited

OTHER PUBLICATIONS

Isabell Begemann et al.; Correlative Light Electron Microscopy: Connecting Synaptic Structure and Function, Frontiers in Synaptic Neuroscience, vol. 8, Aug. 23, 2016, p. 28.

Scopsi L et al.; Increased sensitivity in peroxidase immunocytochemistry. A comparative study of a number of peroxidase visualization methods employing a model system, Histochemistry, Springer International, DE, vol. 84, No. 3, May 1, 1986, pp. 221-230.

METHOD FOR IMAGING A BIOLOGICAL SAMPLE AND CORRESPONDING PROBE

CROSS-REFERENCE TO RELATED PATENT APPLICATIONS

This patent application is a continuation of PCT/IT2018/050142, filed Jul. 27, 2018, which claims priority to Italian Application No. 102017000087291, filed Jul. 28, 2017, the entire teachings and disclosure of which are incorporated herein by reference thereto.

FIELD OF THE INVENTION

Formulations of the present invention concern a method for imaging a biological sample using imaging probes usable in microscopy, in particular in fluorescence optical microscopy, electron microscopy, or in correlative microscopy (CLEM correlative light electron microscopy).

Here and hereafter, by imaging we mean the acquisition of images of a biological sample or a part of it, such as cells for example, in which it is possible to identify the imaging probes and/or possible molecules associated with them.

The present invention also concerns the imaging probes used to perform experiments on a biological sample by microscopy, such as for example immunocytochemistry experiments, or experiments to identify specific molecules of interest.

BACKGROUND OF THE INVENTION

One of the main microscopy techniques in the biological field is CLEM, because it allows to visualize, identify and follow the movement of specific molecules in a biological sample on a spatial scale normally defined by tens of microns to a few nanometers.

This technique combines the advantages of fluorescence optical microscopy (FOM) with those of transmission electron microscopy (TEM), so as to be able to locate the specific molecule of interest in the biological sample with high precision.

Other electron microscopy techniques provide to perform immunocytochemical experiments, also called immunogold in this specific field, to localize specific antigens in the biological sample on a nanometric scale.

In these experiments, probes are used that typically consist of colloidal gold nanoparticles conjugated with antibodies or proteins able to recognize and bond with specific antigens.

In this context, it becomes necessary to be able to have probes available that can be used both for CLEM and also to perform immunocytochemical experiments that make the specific molecules detectable with high precision, without generating artifacts and/or alterations in the biological sample.

Probes consisting of quantum dots or quantum rods are known, or combinatorial probes consisting of a fluorophore conjugated with electron-dense nanoparticles, such as nanoparticles of gold having a diameter of about 1 nm, also called "NanoGolds" in this specific field.

Although such probes are able to penetrate inside individual cells possibly present in the biological sample, they are difficult to detect using TEM and require an accretion passage known as silver or gold enhancement.

This accretion passage requires the use of a solution of silver or gold salts in the presence of one or more reducing agents which entail the addition of an aspecific contribution which renders the interpretation of the images obtained problematic.

Other CLEM probes exploit the fluorescence of the molecules associated with them in order to photo-convert diaminobenzidine (DAB), a derivative of benzidine, into DAB polymers that form an osmiophilic precipitate clearly visible for the TEM.

However, if a double immunolocalization by electron microscopy is to be performed, these probes require the use of complexes consisting of avidin and biotinylated peroxidase which, by bonding with the primary antibody, oxidize the DAB, making it osmiophilic and therefore visible for the TEM.

This is expensive both from the energy point of view and from a cost point of view since it requires long performance times.

As an alternative to photo-conversion, DAB osmiophilic polymers can also be produced by peroxidase-conjugated probes, in particular horseradish peroxidase (HRP).

Unlike "NanoGolds", the HRP enzyme not only maintains its sizes unchanged, but is also sensitive to pH, temperature and pressure conditions.

This means that the HRP enzyme cannot penetrate inside an individual cell and that it is frequently subject to denaturing in relation to the conditions of the environment in which it is found.

Because of this, it is necessary for the probes conjugated with the HRP enzyme to be kept constantly in a controlled environment.

Some known solutions provide to use inorganic nanoparticles comprising a lattice doped with luminescent ions able to be coupled with specific molecules to allow them to be detected in the biological sample.

For example, document EP-A-1.801.593 provides to use complex inorganic nanoparticles, such as lattices of inorganic salts, oxides or semiconductors hosting rare earth cations or transition metals that activate luminescence.

Because of the large sizes compared to the typical sizes of the components of the biological sample, these known lattices can potentially interfere both with the specific molecule associated with them and with the biological sample itself.

Furthermore, these known lattices typically have high levels of toxicity and can therefore significantly alter the behavior of the biological sample.

Some of the known imaging methods for biological samples have numerous disadvantages closely correlated to the size, electron density, and toxicity of the probes used.

Probes with a size in the range of a few nanometers or low electron-density are difficult to detect by TEM, while larger probes can significantly interfere with the antigen-protein activity which does not allow to obtain images without artefacts and/or alterations.

These problems are even more evident in the case where it is intended to detect two different proteins simultaneously, in which pairs of probes of increasing sizes or specific complexes are used.

There is therefore a need to perfect and make available an imaging method for a biological sample which overcomes at least one of the disadvantages of the state of the art.

There is also the need to perfect and make available an imaging probe which can be used to obtain images of a biological sample which overcomes at least one of the disadvantages of the state of the art.

The present invention is intended to provide an imaging method able to obtain images in which specific molecules can easily be identified in the biological sample even on a subcellular scale, without it being necessary to perform silver or gold enhancement, or to use complexes.

It is also a purpose of the present invention to provide an imaging probe which allows to obtain images both by means of CLEM, and also by performing immunocytochemical experiments that are not altered and/or free from artifacts.

It is another purpose of the present invention to provide an imaging probe that has low toxicity and is stable over a wide range of pH, temperatures and pressures, without it being kept in a controlled environment.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

Embodiments described here concern a method for imaging a biological sample using microscopy, such as, by way of preferential example, fluorescence optical microscopy, electron microscopy, correlative microscopy, ion beam microscopy, electromagnetic radiation microscopy, and combinations thereof.

In accordance with one aspect of the present invention, the method provides to use in the biological sample nanoparticles of platinum, an oxidizing agent and an oxidizable substrate capable of producing an electron-dense osmiophilic precipitate localized around the nanoparticles of platinum.

According to the present invention, the osmiophilic precipitate is obtained by oxidizing the oxidizable substrate activated by the nanoparticles of platinum and by the oxidizing agent.

This solution allows to perform both CLEM and immunocytochemical experiments, possibly functionalizing the nanoparticles of platinum with biological molecules and/or molecules able to emit fluorescence, that is, fluorescent markers.

Applicant has found that nanoparticles of platinum have an intrinsic and high peroxidase activity which in the presence of an oxidizable substrate and an oxidizing agent, such as for example hydrogen peroxide, activate the oxidation of the oxidizable substrate and generate an osmiophilic precipitate around the nanoparticles of platinum.

The osmiophilic precipitate has a high electron-density that allows it to amplify the signal in electron microscopy and therefore make the nanoparticles of platinum clearly visible even at low enlargements and on ample field views.

Applicant has found that the amplification of the signal in electron microscopy relating to the nanoparticles of platinum is about one order of magnitude greater than the signal obtainable with gold nanoparticles having the same size but, as is known, more electron-dense.

This greatly simplifies the correlation between electron microscopy images with corresponding fluorescence images, which is currently a key point in the field of correlative microscopy.

Thanks to the amplification of the signal it is possible to detect nanoparticles of platinum with sizes even of about 1 nm inside cells possibly present in the biological sample, without it being necessary to perform the accretion of the nanoparticles through silver or gold enhancement.

According to the present invention it is therefore possible to use nanoparticles of platinum less electron-dense than nanoparticles of gold in order to perform imaging of a biological sample.

According to possible solutions, the oxidizable substrate comprises at least one chemical compound chosen from a group consisting of: 3,3',5,5'-tetramethylbenzidine (TMB), 3,3'-diaminobenzidine (DAB), p-phenylenediamine-pyrocatechol and homovanillic acid.

According to possible embodiments, the oxidizing agent is chosen from a group consisting of: hydrogen peroxide, tert-butyl peroxide, tert-butyl hydroperoxide, peracetic acid, benzoyl peroxide, isopropylbenzene hydroperoxide, arachidonic acid 5-hydroperoxide and dodecyl 2-methoxypropan-2-il peroxide.

According to possible embodiments, the oxidizing agent is hydrogen peroxide.

Depending on the oxidizing agent chosen, it is possible to define the oxidation times and the degree of oxidation required in relation to the specific needs on each occasion.

In accordance with possible embodiments, the nanoparticles of platinum are bonded directly or indirectly with at least one related molecule able to bond, in its turn, with a specific substance present in the biological sample, said related molecule being chosen from a group consisting of: an antibody, a protein, an aptamer, a peptide, a sugar, a polysaccharide, a biological molecule and a chemical compound.

Applicant has found that the nanoparticles of platinum can be functionalized with specific related molecules, or fluorochromes, without the latter compromising the peroxidase activity of the nanoparticles of platinum.

Nanoparticles of platinum not only have low cytotoxicity, but also the advantage of not requiring complex surface functionalizations or bioconjugation procedures.

Moreover, unlike the HRP enzyme, the possibly functionalized nanoparticles of platinum have a high stability in a wide range of pH, temperature and pressure.

This allows to preserve the nanoparticles even at ambient temperature and without the need to resort to systems for maintaining defined environmental conditions.

According to possible embodiments, the method provides to use nanoparticles of gold and/or silver in the biological sample, directly or indirectly bonded with at least a related molecule which is different from at least one of the related molecules bonded with the nanoparticles of platinum.

Using nanoparticles of platinum and nanoparticles of gold and/or silver respectively with and without peroxidase activity, it is possible to recognize two related molecules, for example two proteins, associated with them by the different signal produced by the former with respect to the others.

In the context of the present invention, the possibility of carrying out simultaneous double localizations of two related molecules in a biological sample means that small probes can be used, since the risk of possible interferences of the probe on the protein of interest is considerably reduced.

Formulations of the present invention also concern an imaging probe able to be detected in a biological sample by means of microscopy, such as by way of preferential example, fluorescence optical microscopy, electron microscopy, correlative microscopy, ion beam microscopy, electromagnetic radiation microscopy, and combinations thereof.

In accordance with one aspect of the present invention, the probe comprises nanoparticles of platinum, an oxidizing agent and an oxidizable substrate.

The nanoparticles of platinum and the oxidizing agent are configured to activate the oxidation of the oxidizable substrate to obtain an electron-dense osmiophilic precipitate localized around the nanoparticles of platinum.

BRIEF DESCRIPTION OF THE DRAWINGS

These and other characteristics of the present invention will become apparent from the following description of some embodiments, given as a non-restrictive example with reference to the attached drawings wherein.

DETAILED DESCRIPTION OF SOME EMBODIMENTS

Figure 2:
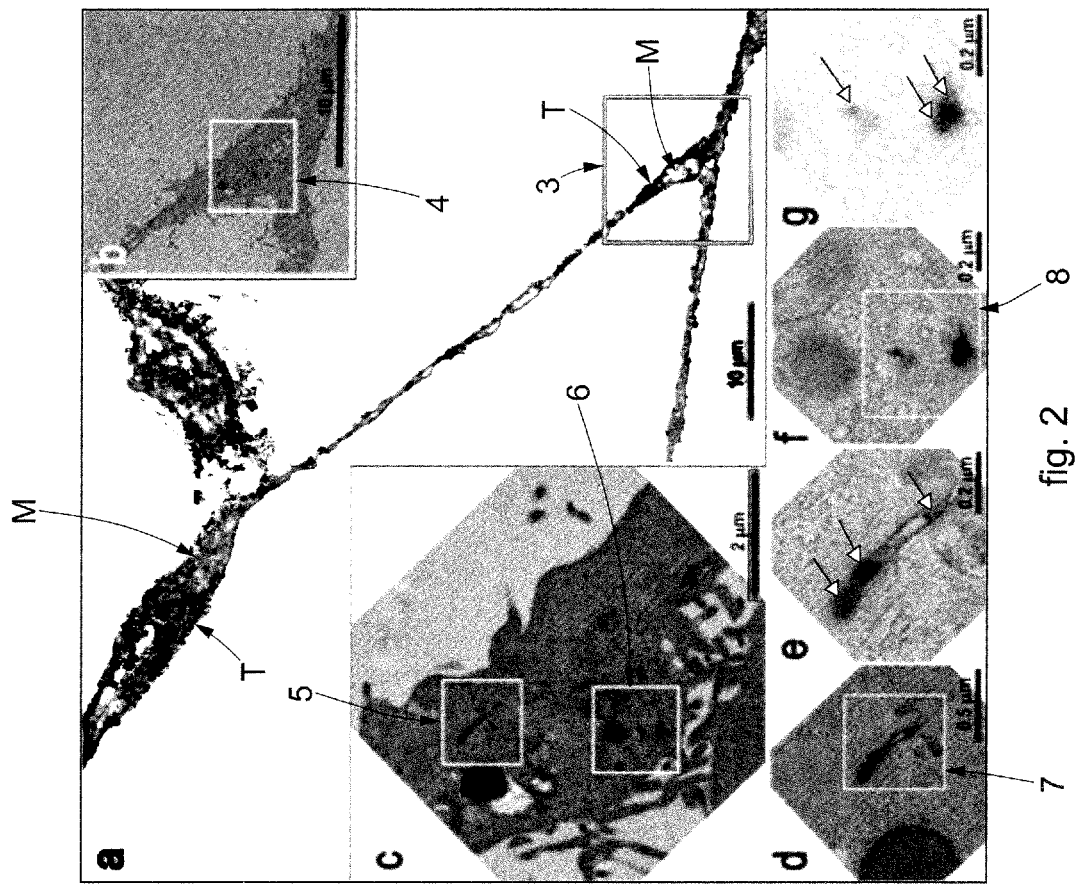
FIG. 2 shows a series of CLEM images (the square marked by the letter "a" refers to a FOM image, and the squares marked by the letters "b" to "g" refer to TEM images) with increasing enlargements of a biological sample obtained according to one of the possible embodiments described of the imaging method according to the present invention.

Embodiments described here concern a method for imaging a biological sample to obtain at least an image of at least part of the biological sample in which it is possible to detect the specific molecules of interest on each occasion.

The imaging method provides to use in the biological sample imaging probes able to be detected by microscopy.

According to possible solutions, microscopy is chosen from a group consisting of: fluorescence optical microscopy, electron microscopy, correlative microscopy, ion beam microscopy, electromagnetic radiation microscopy, and combinations thereof.

By way of non-restrictive example, the imaging probes according to the present invention can be used both for CLEM and also to perform immunocytochemical experiments, or immunogold experiments.

According to the present invention, the imaging method provides to use in the biological sample imaging probes consisting of nanoparticles of platinum, an oxidizing agent and an oxidizable substrate.

According to possible solutions, the oxidizable substrate can comprise one or more chromogenic and/or oxidizing molecules.

Nanoparticles of platinum can be intrinsically fluorescent, or bonded with molecules able to emit fluorescence, such as fluorophores and/or fluorescent markers for example.

The intrinsic fluorescence of nanoparticles of platinum is related to the size of the nanoparticles of platinum, as they can emit electromagnetic radiation by fluorescence in relation to specific defined sizes.

In accordance with possible solutions, the nanoparticles of platinum have sizes equal to or less than 100 nm.

According to possible solutions, the nanoparticles of platinum have sizes comprised between 0.5 nm and 20 nm.

According to possible solutions, the nanoparticles of platinum have sizes comprised between 2 nm and 10 nm.

These ranges in size not only include the specific sizes for which the nanoparticles of platinum are intrinsically fluorescent, but are also such as to allow the nanoparticles of platinum to penetrate into possible cells present in the biological sample.

As will be clear hereafter, this is advantageous in terms of spatial resolution and costs, as it allows to obtain images on subcellular scales without the aid of silver or gold enhancement.

According to the present invention, the imaging probe is based on the peculiar and intrinsic peroxidase activity of nanoparticles of platinum, in particular having such sizes.

According to possible variant embodiments, nanoparticles of platinum can constitute nanoclusters of nanoparticles, that is, agglomerates of nanoparticles of platinum.

Applicant has found that nanoparticles of platinum are able to catalyze the reduction of the oxidizing agent, such as for example hydrogen peroxide in water, using an oxidizable substrate, thus promoting the generation of an osmiophilic precipitate localized around the nanoparticles of platinum.

This osmiophilic precipitate is clearly visible under an electron microscope because it has a high electron-density.

Thanks to the localization of the osmiophilic precipitate induced by the surface peroxidase activity of the nanoparticles of platinum, it is possible to exploit the electron-dense contribution of the osmiophilic precipitate to localize the nanoparticles of platinum in the biological sample.

Applicant has found that the peroxidase activity of nanoparticles of platinum is much higher than that of natural peroxidase enzyme in molar terms and, unlike the latter, nanoparticles of platinum are extremely stable in wide ranges of pH, temperature and pressure.

According to possible embodiments, the oxidizable substrate comprises at least one chemical compound selected from a group consisting of: 3,3',5,5'-tetramethylbenzidine (TMB), 3,3'-diaminobenzidine (DAB), p-phenylenediamine-pyrocatechol, and homovanillic acid.

According to possible solutions, the substrate can comprise other benzidine derivatives.

According to possible embodiments, the oxidizing agent is selected from a group consisting of: hydrogen peroxide, tert-butyl peroxide, tert-butyl hydroperoxide, peracetic acid, benzoyl peroxide, isopropylbenzene hydroperoxide, arachidonic acid 5-hydroperoxide and dodecyl 2-methoxypropan-2-il peroxide.

According to possible preferential solutions, the oxidizing agent is hydrogen peroxide.

According to possible embodiments, the nanoparticles of platinum can also be surface functionalized, that is, they can be directly or indirectly bonded with at least one related molecule.

By related molecule we mean a molecule able to bond, in its turn, with a specific substance present in the biological sample.

According to possible solutions, the related molecule is chosen from a group consisting of: an antibody, a protein, an aptamer, a peptide, a sugar, a polysaccharide, a biological molecule, and a chemical compound.

This property does not affect peroxidase activity and allows the formation of complex systems consisting of nanoparticles externally functionalized with antibodies and/or proteins, which can be used to identify, for example, specific antigens using FOM and/or TEM.

This makes it possible to use the imaging probes both in CLEM experiments and also to perform immuno-cytochemical experiments.

Another possibility offered by the imaging probes according to the present invention is to monitor inside the biological sample the dynamics of nanoparticles of platinum even smaller than 10 nm, which nowadays are difficult to visualize through electron microscopy techniques.

The actual efficacy of nanoparticles of platinum as imaging probes both for CLEM and for immuno-cytochemical experiments has been experimentally tested by Applicant.

To test the actual amplification of the electron-dense signal produced by the peroxidase activity of nanoparticles of platinum, Applicant used nanoparticles of platinum of various sizes inside a biological sample, in the presence of a DAB substrate and hydrogen peroxide.

It is clear that modifications and/or additions of parts can be made to the imaging method and to the imaging probe described heretofore, without departing from the field of the present invention.

It is clear that also the use of nanoparticles of platinum, an oxidizing agent and an oxidizable substrate to obtain an electron-dense osmiophilic precipitate localized around said nanoparticles of platinum as an imaging probe according to any of the embodiments described to implement an imaging method for a biological sample using microscopy as in any of the embodiments described, is comprised in the field of protection of the present invention.

It is also clear that, although the present invention has been described with reference to some specific examples, a person of skill in the art will certainly achieve many other equivalent forms of the imaging method and imaging probe having the characteristics set forth in the claims and therefore all coming within the field of protection defined thereby.

We will now describe some example and non-restrictive embodiments of implementing the imaging method in accordance with the present description.

EXAMPLE 1

Figure 1:
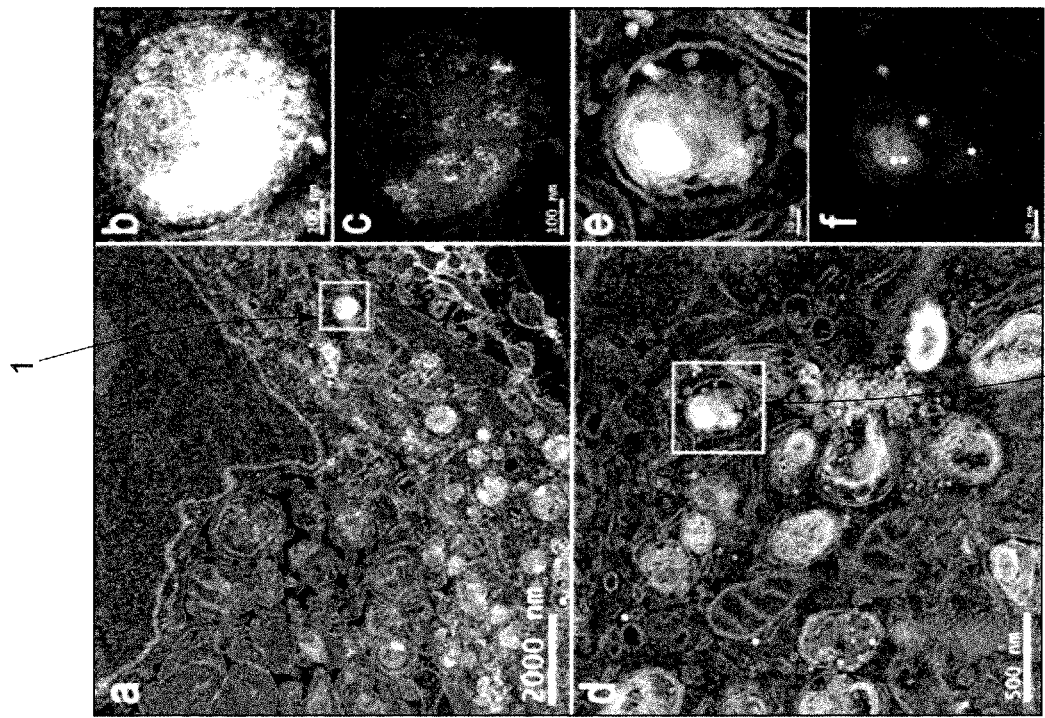
FIG. 1 shows two groups of images (the squares marked by the letters "a" to "c" refer to the first group and the squares marked by the letters "d" to "f" refer to the second group) with increasing enlargements of two biological samples obtained according to one of the possible embodiments described of the imaging method according to the present invention.

To test the actual amplification of the electron-dense signal produced by the peroxidase activity of nanoparticles of platinum in a biological sample inside the cells, in the example shown in FIG. 1 a biological sample containing tumor cell lines (HeLa) was incubated with imaging probes having nanoparticles of platinum of 4 nm and 10 nm.

The images shown in the squares of FIG. 1 were obtained through electron microscopy, in particular acquired by HAADF (high angular annular dark field detector) scanning TEM (STEM), where the squares "b" and "c" are enlargements of the area 1 highlighted in square "a" and squares "e" and "f" are enlargements of the area 2 highlighted in square "d".

With reference to FIG. 1, Applicant has observed, for all the dimensional classes of nanoparticles of platinum used, a considerable increase in the electron-dense signal, which made it possible to identify them even at low enlargement (squares "a" and "d").

The images of FIG. 1 acquired clearly show how it is possible already at low enlargement to identify in the cytoplasm of cells incubated with nanoparticles of platinum of 4 nm (square "a") and 10 nm (square "d") highly electron-dense compartments.

This proves that the nanoparticles of platinum with the oxidizable agent, following the activation of the oxidation of the oxidizable substrate, are surrounded by a large electron-dense region which corresponds to the signal of the osmiophilic precipitate in this case consisting of DAB polymers.

By acting on the parameters of the electron microscope it is possible to optimize the contrast in order to highlight the individual nanoparticles of platinum (squares "c" and "f").

EXAMPLE 2

In the example of FIG. 2, the efficacy was tested of the imaging probes by CLEM to visualize the endosomal pathway of transferrin inside cells.

In the example shown, the nanoparticles of platinum were bioconjugated with a specific protein, that is, with fluorescent transferrin, suitably functionalizing the surface of the nanoparticles of platinum.

In particular, this allowed to create an amide bond between the amino groups present on the surface of the protein and the carboxyl groups present on the surface of the nanoparticles of platinum.

With reference to the square marked by the letter "a" in FIG. 2, the fluorescent signal of the nanoparticles of platinum bioconjugated with fluorescent transferrin is clearly recognizable for the FOM, indicated in black and with the reference "T", while the mitochondria are indicated in gray and with the reference "M".

The localization observed using FOM was confirmed in TEM using the amplification procedure described above.

It should be considered that area 3 is enlarged and visualized using TEM and is shown in square "b".

Square "c" is an enlargement of area 4, while squares "d" and "f" are two enlargements of area 5 and area 6 respectively. Squares "e" and "g" are two enlargements of area 7 and area 8 respectively.

In fact, the TEM analysis of the regions of interest identified by the FOM reveals the presence of an intense electron-dense signal recognizable even at low enlargement (squares "b" and "c" in FIG. 2).

Higher enlargement TEM images show the presence of individual nanoparticles of platinum inside the electron-dense regions (squares "e" and "g" indicated by the arrows).

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for imaging a biological sample using microscopy, wherein the method uses in said biological sample nanoparticles of platinum, an oxidizing agent and an oxidizable substrate to obtain an electron-dense osmiophilic precipitate localized around said nanoparticles of platinum, said osmiophilic precipitate being obtained by means of an oxidation phase of said oxidizable substrate activated by said nanoparticles of platinum and by said oxidizing agent.

2. The method as in claim 1, wherein said oxidizable substrate comprises at least a chemical compound chosen from a group consisting of: 3,3',5,5'-tetramethylbenzidine (TMB), 3,3'-diaminobenzidine (DAB), p-phenylenediamine-pyrocatechol, and homovanillic acid.

3. The method as in claim 1, wherein said oxidizing agent is chosen from a group consisting of: hydrogen peroxide, tert-butyl peroxide, tert-butyl hydroperoxide, peracetic acid, benzoyl peroxide, isopropylbenzene hydroperoxide, arachidonic acid 5-hydroperoxide and dodecyl 2-methoxypropan-2-il peroxide.

4. The method as in claim 1, wherein said oxidizing agent is hydrogen peroxide.

5. The method as in claim 1, wherein said nanoparticles of platinum are bonded directly or indirectly with at least one related molecule able to bond, in its turn, with a specific substance present in said biological sample, said related molecule being chosen from a group consisting of: an antibody, a protein, an aptamer, a peptide, a sugar, a polysaccharide, a biological molecule and a chemical compound.

6. The method as in claim 5, wherein nanoparticles of gold and/or silver are used in said biological sample, directly or indirectly bonded with at least a related molecule which is different from at least one of said related molecules bonded with said nanoparticles of platinum.

7. The method as in claim 1, wherein said nanoparticles of platinum have sizes equal to or smaller than 100 nm.

8. The method as in claim 1, wherein said microscopy is chosen from a group consisting of: fluorescence optical microscopy, electron microscopy, correlative microscopy, ion beam microscopy, electromagnetic radiation microscopy, and combinations thereof.

9. An imaging probe able to be detected in a biological sample using microscopy to implement an imaging method as in claim 1, wherein the imaging probe comprises nanoparticles of platinum, an oxidizing agent and an oxidizable substrate, said nanoparticles of platinum and said oxidizing agent being configured to activate the oxidization of said oxidizable substrate in order to obtain an electron-dense osmiophilic precipitate localized around said nanoparticles of platinum.

10. The imaging probe as in claim 9, wherein said oxidizable substrate comprises at least a chemical compound chosen from a group consisting of: 3,3',5,5'-tetramethylbenzidine (TMB), 3,3'-diaminobenzidine (DAB), p-phenylenediamine-pyrocatechol, and homovanillic acid.

11. The imaging probe as in claim 9, wherein said oxidizing agent is chosen from a group consisting of: hydrogen peroxide, tert-butyl peroxide, tert-butyl hydroperoxide, peracetic acid, benzoyl peroxide, isopropylbenzene hydroperoxide, arachidonic acid 5-hydroperoxide and dodecyl 2-methoxypropan-2-il peroxide.

12. The imaging probe as in claim 9, wherein said oxidizing agent is hydrogen peroxide.

13. The imaging probe as in claim 9, wherein said nanoparticles of platinum are bonded directly or indirectly with at least one related molecule able to bond, in its turn, with a specific substance present in said biological sample, said related molecule being chosen from a group consisting of: an antibody, a protein, an aptamer, a peptide, a sugar, a polysaccharide, a biological molecule and a chemical compound.

14. Use of nanoparticles of platinum, an oxidizing agent and an oxidizable substrate to obtain an electron-dense osmiophilic precipitate localized around said nanoparticles of platinum to implement a method for imaging a biological sample using microscopy utilizing an imaging probe as in claim 9.

15. Use of nanoparticles of platinum, an oxidizing agent and an oxidizable substrate to obtain an electron-dense osmiophilic precipitate localized around said nanoparticles of platinum as an imaging probe, to implement a method for imaging a biological sample utilizing microscopy according to claim 1.

* * * * *